United States Patent [19]

Jorgensen et al.

[11] Patent Number: 5,650,331

[45] Date of Patent: Jul. 22, 1997

[54] OPTICAL HIGH ACIDITY SENSOR

[75] Inventors: Betty S. Jorgensen, Jemez Springs; Howard L. Nekimken, Los Alamos, both of N. Mex.; W. Patrick Carey, Lynnwood, Wash.; Patrick E. O'Rourke, Martinez, Ga.

[73] Assignee: The United States of America as represented by the United States Department of Energy, Washington, D.C.

[21] Appl. No.: 770,388

[22] Filed: Oct. 3, 1991

[51] Int. Cl.⁶ ..................................... G01N 21/00
[52] U.S. Cl. ............... 436/163; 436/172; 436/800; 422/55; 422/57; 422/68.1; 356/436
[58] Field of Search ..................... 436/163, 172, 436/800; 422/55, 57, 68, 82.06; 356/412, 410, 414, 411, 436; 8/552, 657

[56] References Cited

U.S. PATENT DOCUMENTS

| | | | |
|---|---|---|---|
| 3,658,542 | 4/1972 | Henry, Jr. et al. | 430/343 |
| 4,066,403 | 1/1978 | Bruschi | 436/170 |
| 4,200,110 | 4/1980 | Peterson et al. | |
| 4,488,814 | 12/1984 | Johnson | 356/414 |
| 4,560,248 | 12/1985 | Cramp et al. | |
| 4,577,109 | 3/1986 | Hirschfeld | 436/172 |
| 4,600,310 | 7/1986 | Cramp et al. | |
| 4,647,210 | 3/1987 | Morris et al. | 356/414 |
| 4,682,895 | 7/1987 | Costello | |
| 4,803,049 | 2/1989 | Hirschfeld et al. | |
| 4,906,249 | 3/1990 | Fogt et al. | |
| 4,973,561 | 11/1990 | Hansen et al. | 356/436 |
| 5,034,189 | 7/1991 | Cox et al. | 436/172 |

OTHER PUBLICATIONS

Carey et al. in Analytical Chemistry, vol. 61, pp. 1674–1678, (1989).

*Primary Examiner*—Laura Edwards
*Attorney, Agent, or Firm*—Bruce H. Cottrell; William Eklund; William R. Moser

[57] ABSTRACT

An apparatus and method for determining acid concentrations in solutions having acid concentrations of from about 0.1 Molar to about 16 Molar is disclosed. The apparatus includes a chamber for interrogation of the sample solution, a fiber optic light source for passing light transversely through the chamber, a fiber optic collector for receiving the collimated light after transmission through the chamber, a coating of an acid resistant polymeric composition upon at least one fiber end or lens, the polymeric composition in contact with the sample solution within the chamber and having a detectable response to acid concentrations within the range of from about 0.1 Molar to about 16 Molar, a measurer for the response of the polymeric composition in contact with the sample solution, and, a comparer of the measured response to predetermined standards whereby the acid molarity of the sample solution within the chamber can be determined. Preferably, a first lens is attached to the end of the fiber optic light source, the first lens adapted to collimate light from the fiber optic light source, and a second lens is attached to the end of the fiber optic collector for focusing the collimated light after transmission through the chamber.

24 Claims, 10 Drawing Sheets

1

OPTICAL HIGH ACIDITY SENSOR

FIELD OF THE INVENTION

The present invention relates to the field of sensors, and more particularly, to the field of fiber optic sensors for the determination of acid concentrations within solutions. This invention is the result of a contract with the Department of Energy (Contract No. W-7405-ENG-36).

BACKGROUND OF THE INVENTION

Acidity measurements of high acid concentrations in solutions are crucial in many industrial applications, e.g., for optimization of metal processing, for the production of bulk acids, for chemical waste-treatment processes, and for recycling acids. Generally, pH electrodes are not useful at pH's below about 1, and especially at negative pH's such as found in concentrated acid solutions. Continuous samplings and subsequent analyses via titration are often required to monitor ongoing processes involving such concentrated acid solutions. Such samplings and analyses waste both time and materials while generating a separate wastestream.

Fiber-optic sensors including polymer coatings upon the fiber optic waveguide have been previously used to determine high acid concentrations. For example, Carey et al. in Anal. Chem., 1989, Vol. 61, pp. 1674-1678, describe coating thin films, preferably less than about 1 micron, of polybenzimidazole upon lengths of the fiber optic elements, the polymer containing indicators such as Chrome azurol-S and methyl violet B, for determination of nitric acid and hydrochloric acid concentrations. Problems with this system included the need to strip cladding from the initial fiber, refractive index problems such as a tendency for light to be directed out of the fiber into the polymer where the polymer had a higher refractive index than the fiber, the need for long lengths of stripped and coated fiber to obtain sensitivity, and the need for an ultra thin coating to keep light from travelling within the polymer, i.e., when the coating is thinner than the wavelength of the light, the light is passed back into the fiber.

Accordingly, an object of this invention is to provide an improved apparatus capable of determining the acid concentration of high molarity acid solutions.

Another object of the invention is to provide a durable apparatus capable of determining the acid concentration of high molarity acid solutions where such determination is capable of being automatically conducted on-line during an industrial process run.

It is a further object of this invention to provide a method of continuously monitoring the acid concentrations within an on-going process.

SUMMARY OF THE INVENTION

To achieve the foregoing and other objects, and in accordance with the purposes of the present invention, as embodied and broadly described herein, the present invention provides an apparatus for determination of acid concentrations of a sample solution including a chamber for interrogation of the sample solution, a fiber optic light source for passing light transversely through the chamber, a fiber optic collector having a light receiving end for receiving the light after transmission through the chamber, a coating of an acid resistant polymeric composition upon at least one of either the light emitting end of the fiber optic light source or the light receiving end of the fiber optic collector, the polymeric composition in contact with the sample solution within the chamber and the polymeric composition having a detectable response to acid concentrations within the range of from about 0.1 Molar to about 16 Molar, means for measuring the response of the polymeric composition in contact with the sample solution, and means for comparing the measured response to predetermined standards whereby the acid molarity of the sample solution within the chamber can be determined. Preferably, the apparatus further includes a first lens attached to the end of the fiber optic light source, the first lens adapted to collimate light from the fiber optic light source, and a second lens attached to the end of the fiber optic collector for focusing the collimated light after transmission through the chamber. The polymeric composition of the apparatus is preferably polybenzimidazole including an indicator capable of undergoing colorimetric changes within the range of acid concentrations from about 0.1 Molar to about 16 Molar, or is selected from the group of poly (phenylquinoline), poly(benzobisthiazole), poly (biphenylquinoline), or poly(phenylquinoxaline) wherein the preferred acid molarity range exhibiting a detectable response is from about 0.1 Molar to about 10.0 Molar.

The present invention further provides a method of measuring the acid concentration of a sample solution including passing a portion of the sample solution into a chamber, passing a light source through a fiber optic light source and transversely through the chamber into a fiber optic collector, wherein either the fiber optic light source or the fiber optic collector is coated upon a fiber end with an acid resistant polymeric composition, the polymeric composition in contact with the sample solution within the chamber and having a detectable response to acid concentrations within the range of from about 0.1 Molar to about 16 Molar for a polymeric composition of polybenzimidazole including an indicator capable of undergoing colorimetric changes within such a range or a detectable response to acid concentrations within the range of from about 0.1 Molar to about 10.0 Molar for polymeric compositions selected from the group consisting of poly(phenylquinoline), poly(benzobisthiazole), poly (biphenylquinoline), or poly(phenylquinoxaline), measuring the response of the polymeric composition in contact with the sample solution, and comparing the measured response to predetermined standards whereby the acid molarity of the sample solution within the chamber can be determined. Preferably, a first lens is attached to the end of the fiber optic light source, the first lens adapted to collimate light from the fiber optic light source, and a second lens is attached to the end of the fiber optic collector for focusing the collimated light after transmission through the chamber. The polymeric composition used in the method is preferably selected from the group of poly(phenylquinoline), poly (biphenylquinoline), or poly(phenylquinoxaline) for acid concentrations within the range of from about 0.1 Molar to about 10.0 Molar, and polybenzimidazole including an indicator capable of undergoing colorimetric changes within the range of acid concentrations from about 0.1 Molar to about 16 Molar.

DETAILED DESCRIPTION

The present invention concerns an apparatus and a method for the determination of acid concentrations in highly acidic solutions. The apparatus and method can be used in an on-line system to continually monitor such acid concentrations in ongoing processes. Generally, the present apparatus and method can be used to determine the acid concentrations for acid containing solutions, e.g., mineral acid solutions such as nitric acid solutions, hydrochloric acid solutions, sulfuric acid solutions, perchloric acid solutions, hydrofluoric acid solutions, chlorosulfonic acid solutions, methanesulfonic acid solutions, and may be used for organic acids such as acetic acid, oxalic acid and the like. The present apparatus and method are especially useful in determining the acid concentrations of high concentration mineral acid solutions, i.e., acid solutions with a pH below one and often for a pH of less than zero.

The apparatus or acid sensor of the present invention involves the use of an acid resistant polymeric composition having a detectable response to acid concentrations within the range of from about 0.1 Molar to about 16 Molar. By "acid resistant" is meant that the polymer composition can be maintained in contact with the solutions of high acid molarity being monitored for time sufficient to measure the acid molarity, and preferably can remain in contact with the solution for extended periods of time without suffering degradation of the polymer or of the detectable response. The polymeric composition is maintained in direct contact with the acidic solution whereupon the detectable response to acid concentrations or changes in acid concentrations can be observed and measured. Such a detectable response can be, e.g., a fluorescent emission, or a colorimetric change, i.e., a change in optical absorption.

The acid resistant polymeric composition of the present invention can be, e.g., from among the group of poly (phenylquinoline), poly(benzobisthiazole), poly (biphenylquinoline), and poly(phenylquinoxaline), each of which undergo a change in fluorescent emission as a function of acid concentrations, can be, e.g., an organic polymer composition as a matrix including an indicator capable of undergoing colorimetric changes within the desired range of acid concentrations or may be an inorganic polymer composition as a matrix including an indicator capable of undergoing colorimetric changes within the desired range of acid concentrations. Examples of organic polymer compositions include polybenzimidazole and polyimide. Examples of inorganic polymer compositions include sol-gel type materials such as metal alkoxides. Preferably, the acid resistant polymeric composition is polybenzimidazole including an indicator capable of undergoing colorimetric changes within the desired range of acid concentrations.

Figure 3:
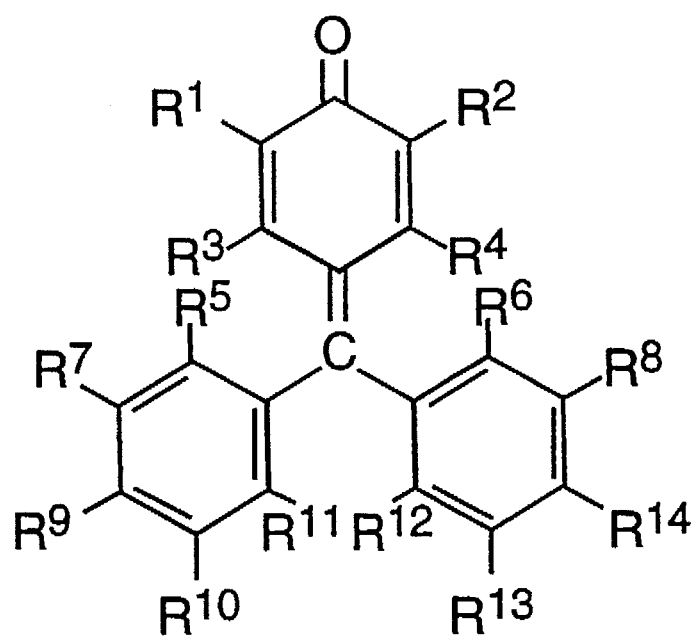
FIG. 3 is a structural representation of indicators useful in the present invention.

Indicators are used to provide selected polymeric compositions, e.g., polybenzimidazole, with a detectable colorimetric change. Among the indicators preferred for inclusion in the polybenzimidazole are those indicators of the class referred to as triarylmethane dyes more particularly triphenylmethane dyes. FIG. 3 illustrates the structure of particularly useful triphenylmethane dye indicators where $R^1$ is methyl, sodium carboxylate, bromo or hydrogen, $R^2$ is methyl, hydroxyl, chloro, bromo, sodium carboxylate or hydrogen, $R^3$ is methyl or hydrogen, $R^4$ is hydrogen, $R^5$ is bromo or hydrogen, $R^6$ is chloro, methyl or hydrogen, $R^7$ is sodium carboxylate, bromo or hydrogen, $R^8$ is sodium sulfonate, bromo, sodium carboxylate, methyl or hydrogen, $R^9$ is hydroxyl, bromo or hydrogen, $R^{10}$ is methyl, bromo or hydrogen, $R^{11}$ is sodium sulfonate or hydrogen, $R^{12}$ is chloro or hydrogen, $R^{13}$ is methyl, hydroxyl, chloro, bromo, an amine, or hydrogen, and $R^{14}$ is hydroxyl or hydrogen. Among the preferred indicators are phenol red and substituted phenol red, e.g., phenol red including substituents such as chloro, bromo, methyl, sodium carboxylate, carboxylic acid, hydroxyl and amines. Common among such substituted phenol red compounds are metacresol purple (metacresolsulfonephthalein), cresol red (ortho-cresolsulfonephthalein), pyrocatecol violet (pyrocatecolsulfonephthalein), chlorophenol-red (3',3"-dichlorophenolsulfonephthalein), xylenol blue (the sodium salt of para-xylenolsulfonephthalein), xylenol orange, mordant blue 3 (C.I. 43820), 3,4,5,6-tetrabromophenolsulfonephthalein, bromoxylenol blue, bromophenol blue (3',3",5',5"-tetrabromophenolsulfonephthalein), bromochlorophenol blue (the sodium salt of dibromo-5',5"-dichlorophenolsulfonephthalein), bromocresol-purple (5',5"-dibromo-ortho-cresolsulfonephthalein), or bromocresol green (3',3",5',5"-tetrabromo-ortho-cresolsulfonephthalein). Other suitable indicators include, for example, Chrome azurol-S (C.I. 43825). Still another suitable indicator is brilliant yellow (C.I. 24890). Blends of indicators can also be used to provide the detectable response, i.e., a detectable colorimetric change.

The useful range for the acid sensor or apparatus of the present invention can vary within the range from about 0.1 Molar to about 16 Molar depending upon the particular indicator used and may further vary depending upon the particular type acid being measured. For example, the preferred range of operation for measuring a nitric acid solution with the sensor employing polybenzimidazole including an indicator of Chrome azurol-S is from about 4 Molar to about 16 Molar. The preferred range of operation for measuring a nitric acid solution with the sensor employing polybenzimidazole including an indicator of phenol red is from about 0.1 Molar to about 4 Molar. The preferred range of operation for measuring a nitric acid solution with the sensor employing polybenzimidazole including an indicator of chlorophenol red is from about 0.4 Molar to about 12 Molar.

Where the polymeric composition includes an indicator, the composition generally includes from about 0.4 percent by weight to about 10 percent by weight of indicator based upon the total weight of the polymer. In one manner of preparing such a polymeric composition, polybenzimidazole can be dissolved in a suitable solvent such as N,N-dimethylacetamide at about a 10 percent by weight to about 15 percent by weight solution, and the indicator subsequently added to the polymer solution in the desired amount. The solution is subsequently applied to the lens by, e.g., dipping, spraying or other suitable means, and the solvent is evaporated.

Polybenzimidazoles are a class of linear polymers whose repeat unit contains a benzimidazole moiety and are commonly known by the acronym PBI. The polybenzimidazoles useful in the polymeric compositions of this invention may comprise any polybenzimidazole resin known to those skilled in the art. Typical polymers of this class and their preparation are more fully described in U.S. Pat. No. 2,895,948, U.S. Pat. No. Reissue 26,065, and in the Journal of Polymer Science, Vol. 50, pages 511–539 (1961), which are herein incorporated by reference.

Examples of polybenzimidazoles include the following:
poly-2,2'-(meta-phenylene)-5,5'-bibenzimidazole;
poly-2,2'-(pyridylene-3",5")-5,5'-bibenzimidazole;
poly-2,2'-(furylene-2", 5")-5,5'-bibenzimidazole;
poly-2,2'-(naphthalene-1",6")-5,5'-bibenzimidazole;
poly-2,2'-(biphenylene-4",4")-5,5'-bibenzimidazole;
poly-2,2'-amylene-5,5'-bibenzimidazole;
poly-2,2'-octamethylene-5,5'-bibenzimidazole;
poly-2,6-(meta-phenylene)-5,5'-diimidazobenzene;
poly-2,2'-cyclohexeneyl-5,5'-bibenzimidazole;
poly-2,2'-(meta-phenylene)-5,5'-di(benzimidazole) ether;
poly-2,2'-(meta-phenylene)-5,5'-di(benzimidazole) sulfide;
poly-2,2'-(meta-phenylene)-5,5'-di(benzimidazole) sulfone;
poly-2,2'-(meta-phenylene)-5,5'-di(benzimidazole) methane;
poly-2,2'-(meta-phenylene)-5,5'-di(benzimidazole) propane-2,2; and,
poly-2,2'-(meta-phenylene)-5,5'-di(benzimidazole) ethylene-1,2 where the double bonds of the ethylene groups are intact in the final polymer.

Figure 2:
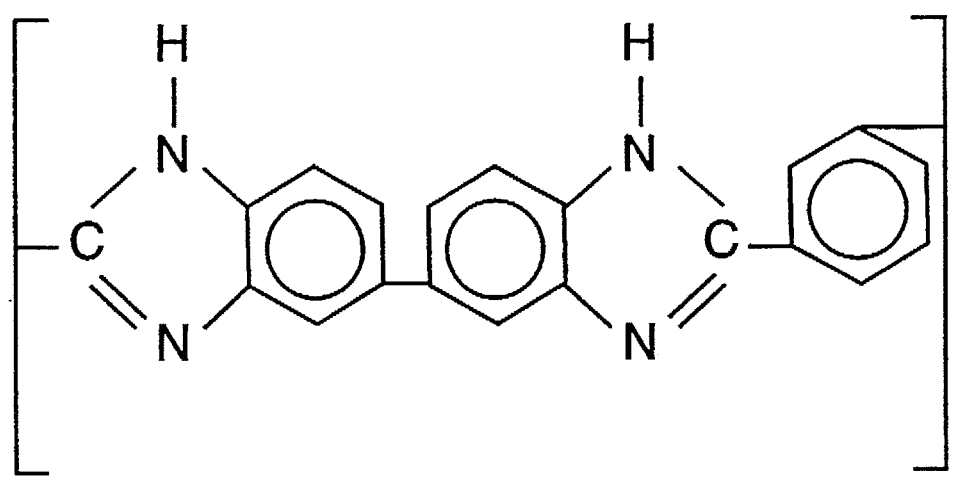
FIG. 2 is a structural representation of a polymer useful in the present invention.

The preferred polybenzimidazole for use in the present invention is one prepared from poly[2,2'-(meta-phenylene) -5,5'-bibenzimidazole], shown in FIG. 2 and available from Hoescht Celanese Corp. The polymer composition may also include a blend of PBI and another acid resistant polymer such as polyimide.

Polyphenylquinoxaline can be used as the polymeric composition and such a polymer is available from Cemota under the tradename of Syntorg IP 200. Polyquinolines such as poly(phenylquinoline) and poly(biphenylquinoline) may be prepared as described in Macromolecules, Vol. 14, pp. 870–880 (1981) and further described in Macromolecules, Vol. 3, no. 3, pp. 496–505 (1981). Poly(benzobisthiazole) may be prepared as described in Macromolecules, Vol. 14, pp. 915–920 (1981).

Figure 1:
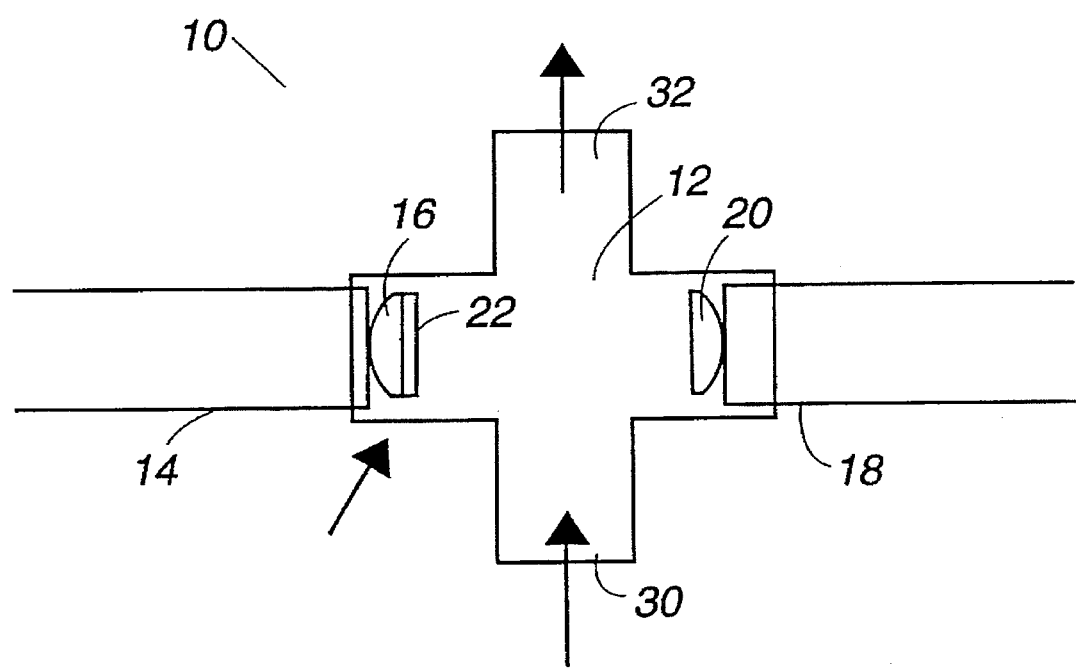
FIG. 1 is a schematic drawing of the apparatus of the present invention.

Referring to FIG. 1, the apparatus 10 of the present invention includes a test chamber 12, e.g., a flow chamber, for interrogation of the sample solution. Such a flow chamber can be, e.g., a side compartment for temporarily diverting a portion of the liquid within a process stream as the acid concentration is measured. In the figure, the solution enters the test chamber 12 at inlet 30 and exits the test chamber 12 at outlet 32. The apparatus of the present invention also includes a fiber optic light source 14 for passing light transversely through the flow chamber. Such a fiber optic light source can be, e.g., a spectrophotometer as a light source, passing through a fiber optic which is linked or coupled to the spectrophotometer. A lens 16 is shown attached to the end of the fiber optic light source, the lens adapted to collimate light from the fiber optic light source prior to the light passing through the solution being measured in the test chamber. A fiber optic collector 18 is situated opposite the fiber optic light source for receiving the collimated light after transmission through the test chamber, e.g., the flow chamber. A second lens 20 is shown attached to the end of the fiber optic collector 18 for focusing the collimated light after transmission through the test chamber 12. At least one of the lens is coated with the polymeric composition and in this case lens 16 includes coating 22. In a preferred arrangement of the test chamber, the flow cell is situated vertically so that any air trapped within the test chamber will rise through the liquid and not become a contaminant in the light path between the lens of the system.

Preferably, lenses 16 and 20 have the curved surfaces facing towards the fiber and the planar surfaces facing towards the sample solution with the polymeric coating 22 upon the planar surface. Such an arrangement can reduce or eliminate dependence of the sensor on the index of refraction of the sample solution.

The lenses used in the present apparatus can be comprised of silica or of sapphire, preferably of silica. The geometry of such lenses necessary to collimate and to collect the light of the fiber optics is well known to those skilled in the art. The polymeric composition of the present invention is applied as a coating upon at least one lens element used in passing light through the sample solution. Generally, the coating upon the lens will be from about 0.1 microns to about 25 microns in thickness, preferably from about 1 micron to about 5 microns in thickness.

A silane coupling agent is used to pretreat the lens prior to applying the polymeric composition. Generally, the silane coupling agent can be a material such as 3-glycidopropyltrimethoxysilane or 3-chloropropyltrimethoxysilane. Other well known silane coupling agents are also suitable.

In the method of the present invention, the output of a spectrophotometer is initially calibrated or referenced with acid solutions of various known molarities. Similarly, for use of the fluorescent emissions, standardization involves calibration or referencing with acid solutions of known molarities. After a calibration, a portion of a target sample solution is passed into a test chamber, followed by passing a light source through, e.g., a lens coated with the desired polymeric composition. The polymeric composition is in contact with the sample solution within the chamber and has a detectable response to acid concentrations within the range of from about 0.1 Molar to about 16 Molar as previously described. By measuring the response of the polymeric composition in contact with the sample solution whether by measuring the fluorescent emissions of the polymeric coating or measuring the colorimetric changes of the polymeric coating and comparing the measured response to previously determined standard responses, such standard responses obtained, e.g., from the initial calibration, the acid molarity of the sample solution within the chamber can be determined. In the case of fluorescent emissions, it may be preferable to receive the fluorescent emissions at a point non-linear with the path of the light from the fiber optic light source, e.g., at a point perpendicular to the path of the light through the test chamber thereby to avoid interference of the fluorescent emissions by the original light source.

Generally, the apparatus and method of the present invention are employed at or near atmospheric pressure and at or near ambient temperatures. Elevated or reduced pressures may also be employed and the temperatures may be varied as desired.

The present invention is more particularly described in the following examples which are intended as illustrative only, since numerous modifications and variations will be apparent to those skilled in the art.

EXAMPLE 1

The flow cell used was a standard, 0.5 inch stainless steel, Swagelok union cross. Optical lenses used were made of 1 centimeter (cm), fused silica rods with approximately 15 millimeter (mm) focal lengths. The lenses, obtained from Antlantic Industrial Optics, had a sub micro A (SMA) fitting for fiber optic coupling. Fiber optic cables of 800 microns in diameter were obtained from Fiberguide, Inc. The spectrophotometer used as the detector was a Quantum 1200 spectrophotometer from LT Industries. The spectrophotometer was run with Spectrometrix software, also from LT Industries using a Texas Microsystems 386 industrial computer. Nitric acid solutions were prepared from concentrated nitric acid, from Baker Industries, and diluted with distilled water. Solutions were introduced into the flow cell with a Micropump gear pump through acid resistant plastic tubing.

A first lens of a lens assembly was initially cleaned in a 1 percent by weight sodium hydroxide solution for about 10 minutes at about 90° C., then in 5 percent by weight hydrochloric acid for about 2 minutes at about 50° C., and finally rinsed with distilled water. The lens was treated with the silane coupling agent prepared by vigorously stirring 0.5 milliliters (ml) of 3-chloropropyltrimethoxysilane, 50 ml of distilled water, and enough glacial acetic acid to maintain a clear homogenous solution, somewhere from about 10 to 20 drops, and 2 ml of isopropanol for about 30 minutes or until clear. The lens was soaked in the coupling agent mixture for about 15 minutes, rinsed with distilled water and heated at about 110° C. for about 30 minutes.

The polymer coating for the lens was prepared as follows. Chrome azurol-S (62 milligrams (mg)) was dissolved into 5 grams of dimethylacetamide. The solution was filtered to remove any undissolved indicator and added to 10 grams of 10 percent by weight polybenzimidazole in dimethylacetamide with stirring. The lens was dipped into the polymer mixture and the excess mixture was drained from the lens by placing the lens onto a paper towel until the solvent was evaporated. The coated lens was then heated at 180° C. for about 4 hours.

The flow cell was mounted upon a ring stand to allow vertical solution flow thereby preventing bubbles from becoming trapped within the flow cell. The source light was from the spectrophotometer's tungsten lamp and was focused into the fiber cable. The light was collimated by the first of two 0.5 inch lenses. This first lens was coated with the polybenzimidazole containing the Chrome azurol-S and the polymer material was in direct contact with the acid solution within the flow cell. The light passed through the polymer coating, through the solution within the flow cell and through a second lens whereby the light was refocused into a second fiber optic cable. From there the light was passed on to the detector on the spectrophotometer.

Figure 4:
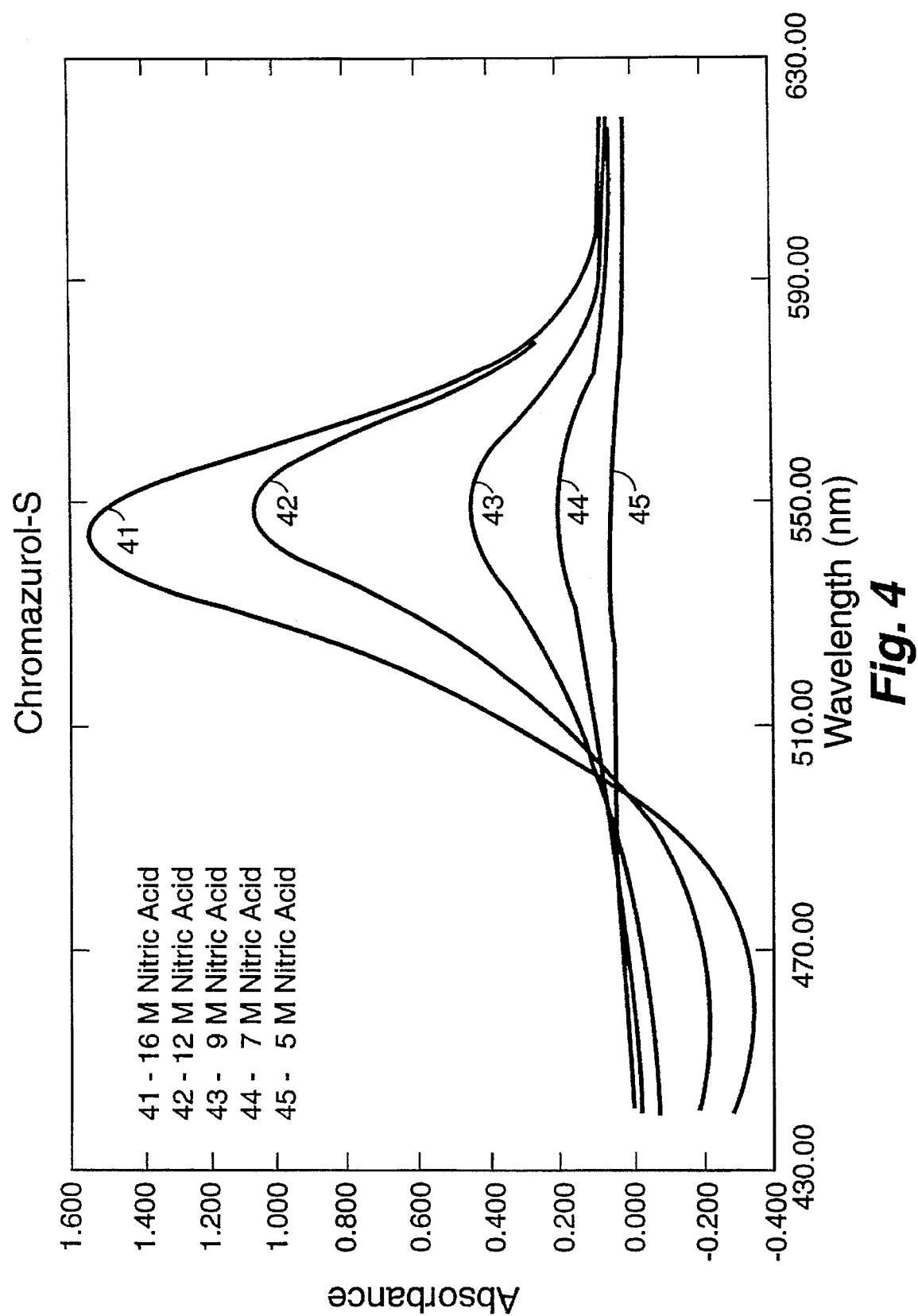
FIG. 4 is a graph of the absorbance versus wavelength for an acid sensor including Chrome azurol-S in polybenzimidazole, such absorbances at various acid concentrations.
Figure 5:
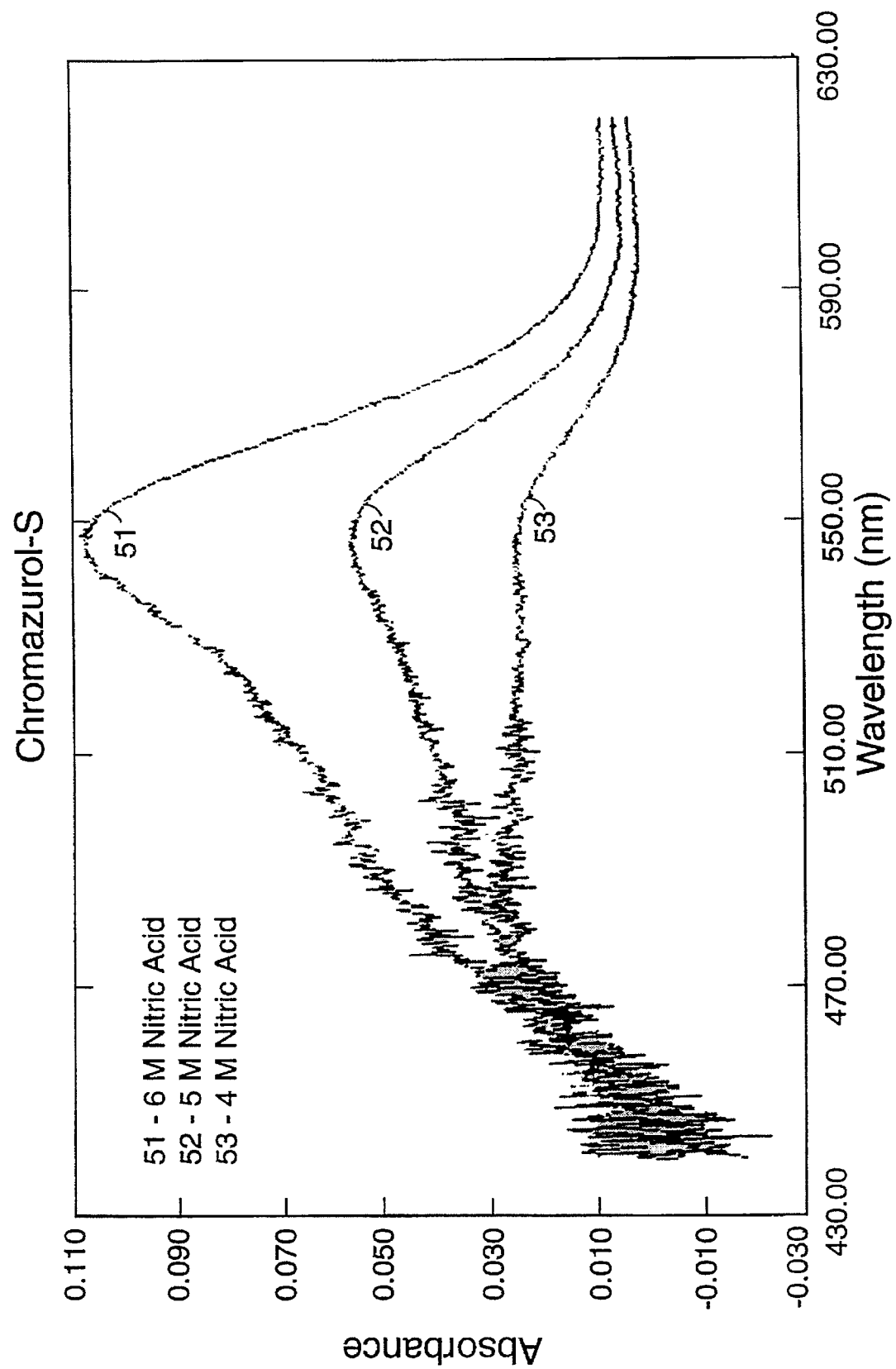
FIG. 5 is a graph of the absorbance versus wavelength for an acid sensor including Chrome azurol-S in polybenzimidazole, such absorbances at various low acid concentrations.

Standard solutions of nitric acid were prepared and run for instrument calibration, i.e., development of a series of absorption traces for the various standard solutions. The standards ranged from 0.4 Molar to 16 Molar. In operation, light was absorbed by the polymer coating with the amount and wavelength of the light absorbed determined by the acidity of the solution. Spectra were obtained as the solution was passed through the flow cell by use of the gear pump at about 10 milliliters per minute. At this flow rate, about 20 spectral scans were obtained and averaged over about 15 seconds for each standard or sample. A reference spectrum from a reference solution of 2.5 Molar nitric acid was subtracted from the spectra for all other acid concentrations, the reference solution being an absorption minimum. The calibration model was then used to determine acid concentration within the unknown solutions. The results of analysis at high acid concentrations are shown in FIG. 4, while analysis at low acid concentrations are shown in FIG. 5. The absorption spectrum maximum was about 550 nanometers (nm).

EXAMPLE 2

Figure 6:
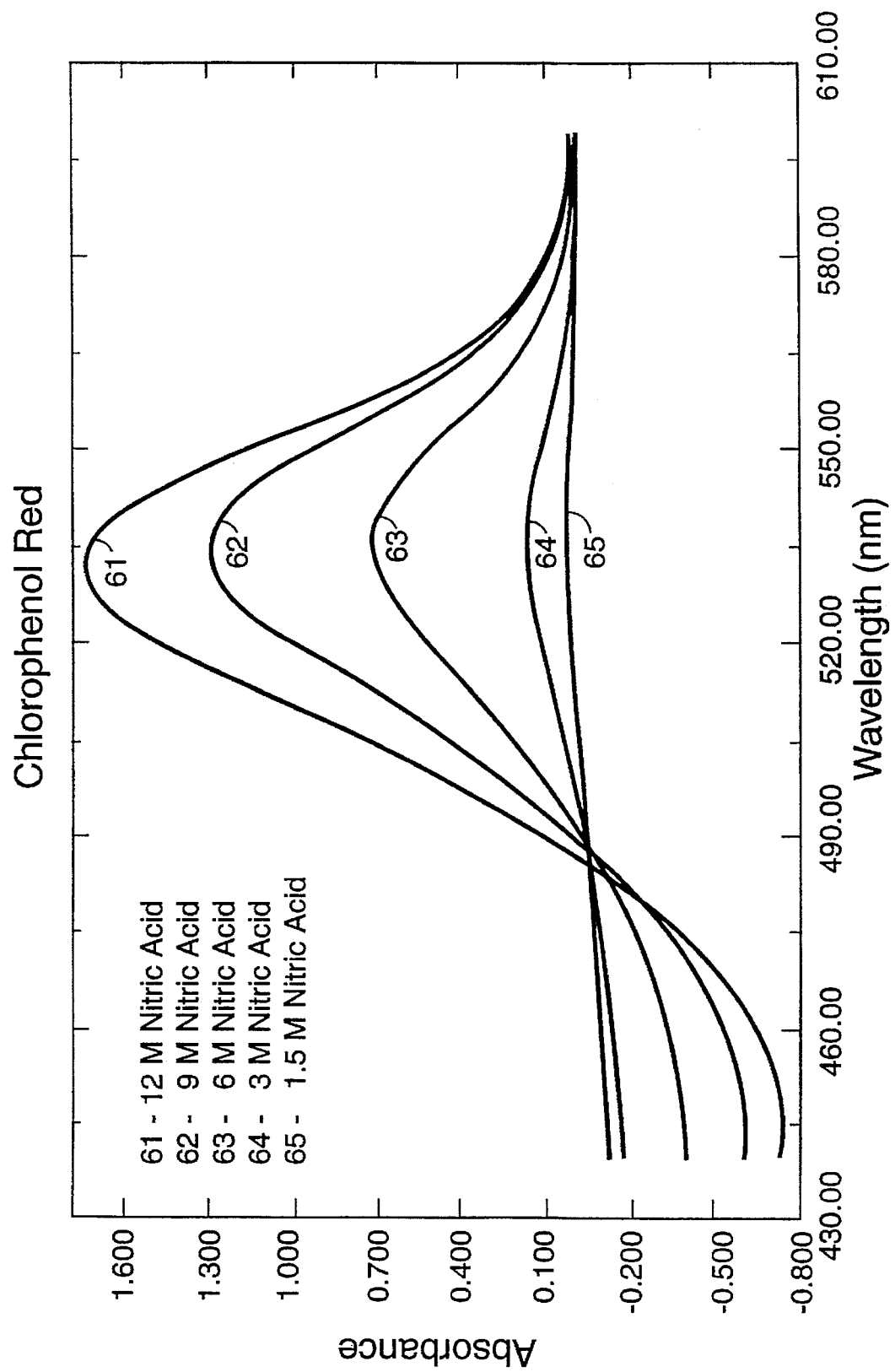
FIG. 6 is a graph of the absorbance versus wavelength for an acid sensor including chlorophenol red in polybenzimidazole, such absorbances at various acid concentrations.
Figure 7:
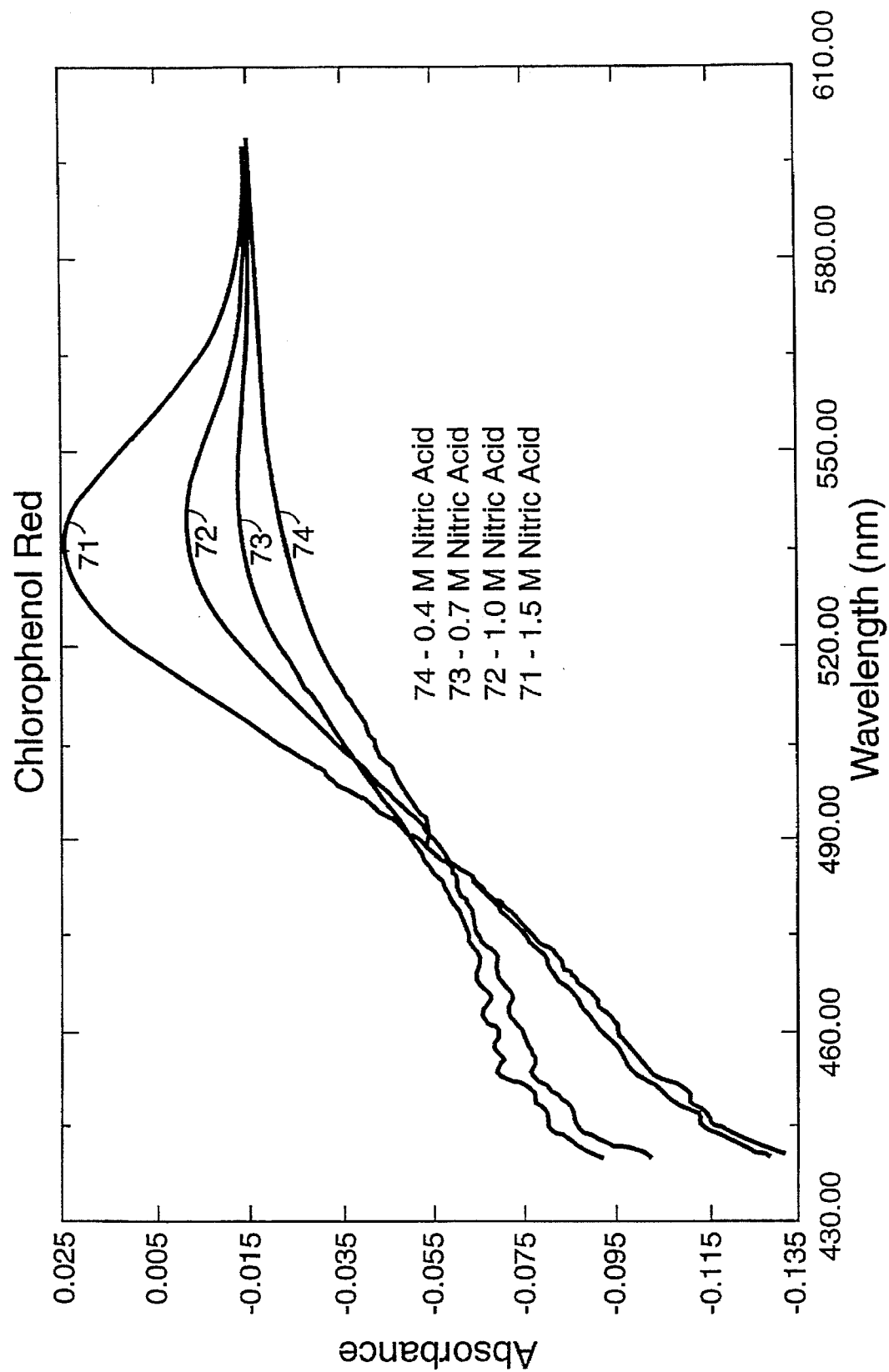
FIG. 7 is a graph of the absorbance versus wavelength for an acid sensor including chlorophenol red in polybenzimidazole, such absorbances at various low acid concentrations.

The lens was prepared and coated as in Example 1 with the following polymer solution. Chlorophenol red (50 mg) was dissolved in 2 ml of dimethylacetamide and then added to 4 grams of 10 percent by weight polybenzimidazole in dimethylacetamide and stirred until it was completely dissolved. The coated lens was heated at 180° C. for about 4 hours. In this example the nitric acid standards were prepared from 0.25 Molar to 12 Molar and the reference solution was 0.25 Molar nitric acid. The results of analysis at various acid concentrations are shown in FIG. 6, while analysis at low acid concentrations are shown in FIG. 7. The absorption spectrum maximum was about 535 nm.

EXAMPLE 3

Figure 8:
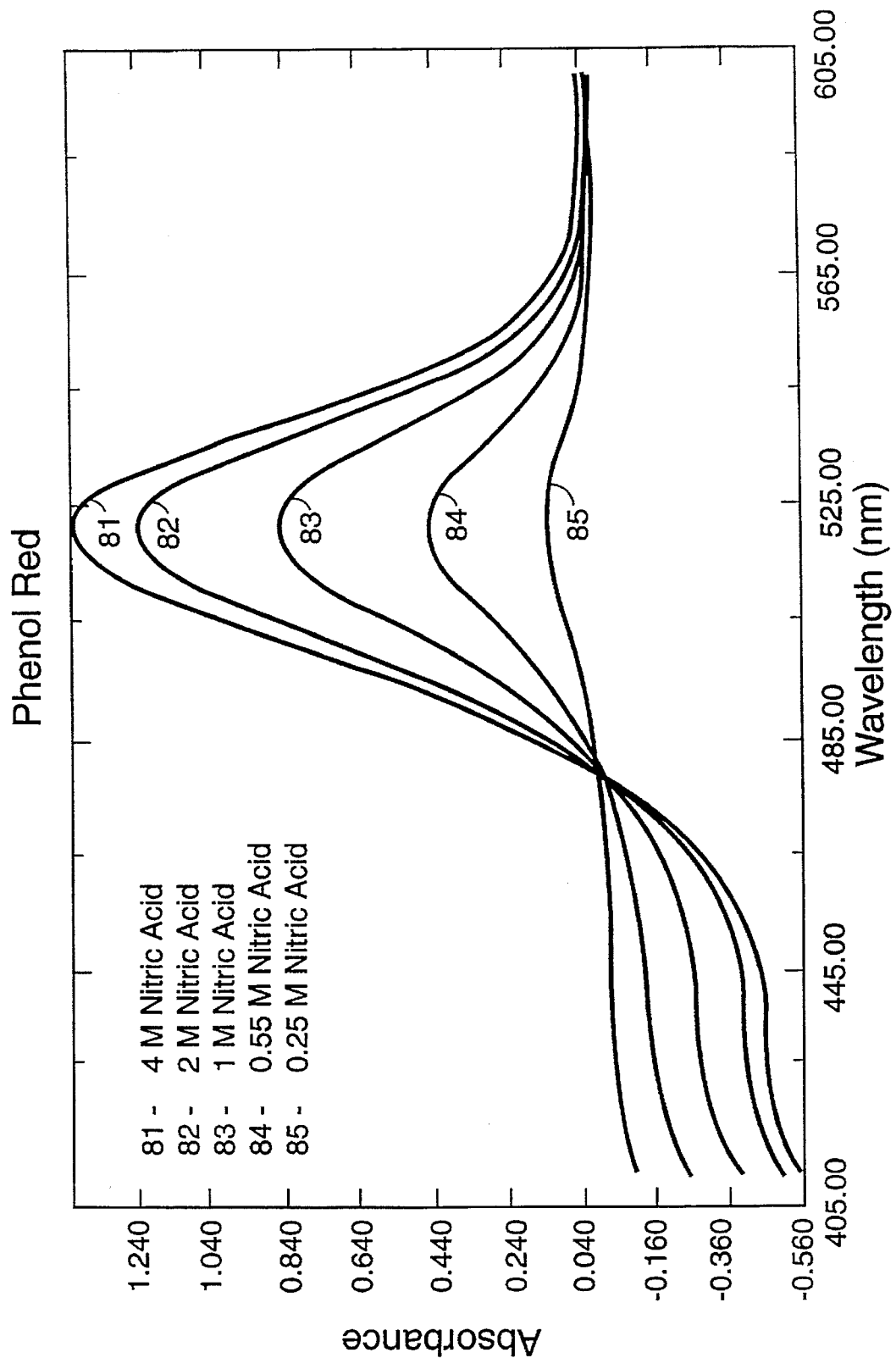
FIG. 8 is a graph of the absorbance versus wavelength for an acid sensor including phenol red in polybenzimidazole, such absorbances at various acid concentrations.

The lens was prepared and coated as in Example 1 with the following polymer solution. Phenol red (50 mg) was added to 5 grams of 10 percent by weight polybenzimidazole in dimethylacetamide and stirred until it was completely dissolved. The coated lens was heated at 180° C. for about 90 minutes. In this example the nitric acid standards were prepared from 0.1 Molar to 4 Molar and the reference solution was 0.1 Molar nitric acid. The results of analysis at various acid concentrations are shown in FIG. 8. The absorption spectrum maximum was about 520 nm.

EXAMPLE 4

A fluorescent polymer is coated onto a lens, pretreated with 3-glycidoxypropyltrimethoxysilane, by first dipping the lens into a 1.0 percent by weight solution of poly (phenylquinoxaline) in chloroform, and then heating the coated lens for about 1 hour at about 110° C.

Standard solutions of nitric acid can then be prepared and run for instrument calibration, i.e., development of a series of absorption traces for the various standard solutions, ranging from about 0.1 Molar to about 10 Molar.

Previous tests with various nitric acid solutions placed upon a poly(phenylquinoxaline) coating, such a coating previously immobilized onto a quartz slide, show a shift in emission spectrum maximum of from about 550 nm in a neutral solution towards shorter wavelengths as the acid solutions become more acidic. The excitation wavelength was 420 nm. The shift in the spectrum begins at about 2.5 Molar nitric acid concentrations. In an acid solution of 8.4 Molar nitric acid, the emission spectrum maximum was about 535 nm.

EXAMPLE 5

The lens is prepared and coated as in Example 1 with the following polymer solution. Brilliant yellow (10 mg) is added to 5 grams of 10 percent by weight polybenzimidazole in dimethylacetamide and stirred until it is completely dissolved. The coated len is heated at 180° C. for about 90 minutes.

Standard solutions of nitric acid can then be prepared and run for instrument calibration, i.e., development of a series of absorption traces for the various standard solutions, ranging from about 1 Molar about to about 12 Molar.

Figure 9:
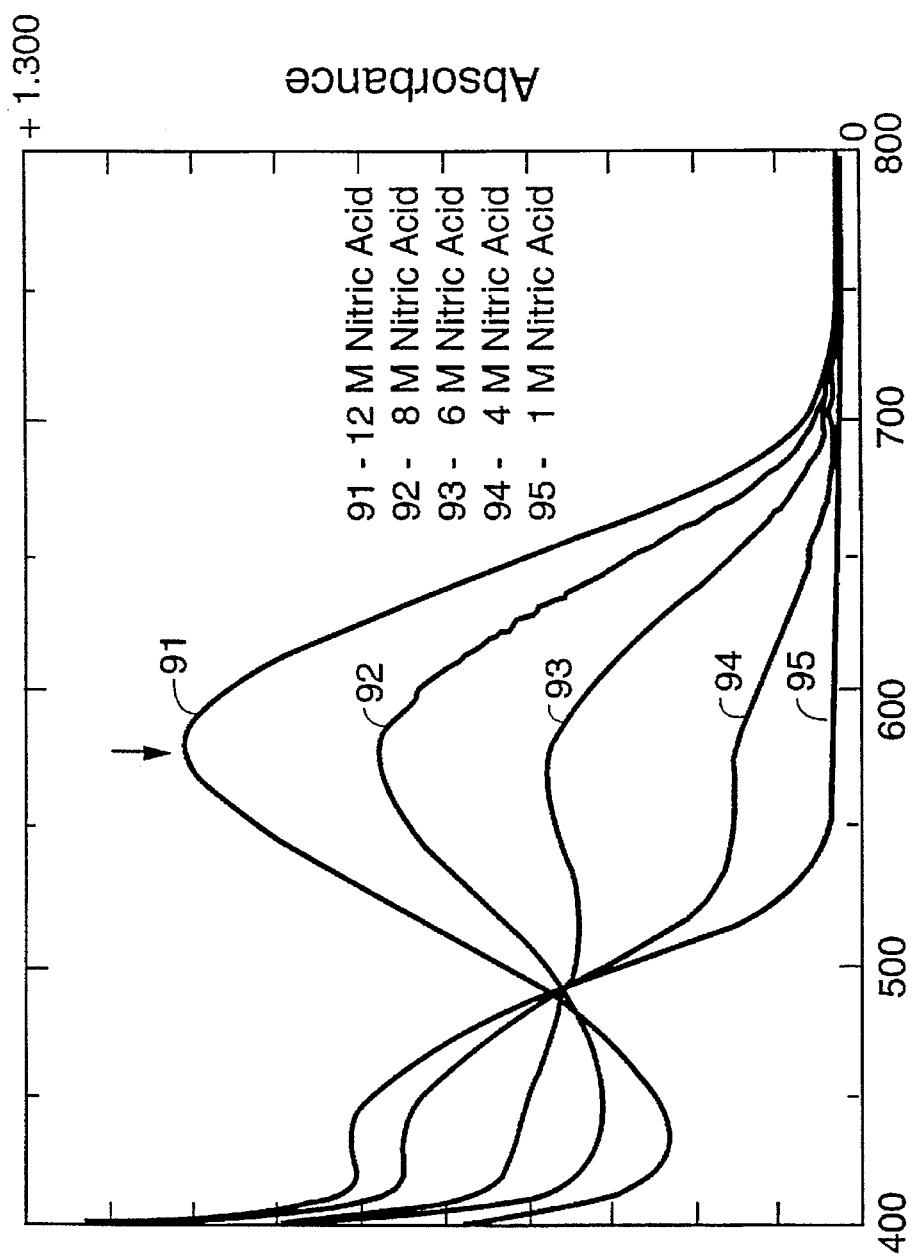
FIG. 9 is a graph of the absorbance versus wavelength for an acid sensor including brilliant yellow in polybenzimidazole, such absorbances at various acid concentrations.

Previous tests with various nitric acid solutions placed upon a brilliant yellow PBI coating, such a coating previously immobilized onto a quartz slide, show an absorption spectrum maximum peak at about 570 nm, such a peak decreasing in intensity at lower acid concentrations. The results of analysis at various acid concentrations are shown in FIG. 9.

EXAMPLE 6

The len is prepared and coated as in Example 1 with the following polymer solution. Brilliant yellow (25 mg) and phenol red (5 mg) are added to 5 grams of 10 percent by weight polybenzimidazole in dimethylacetamide and stirred until they are completely dissolved. The coated len is heated at 180° C. for about 90 minutes.

Figure 10:
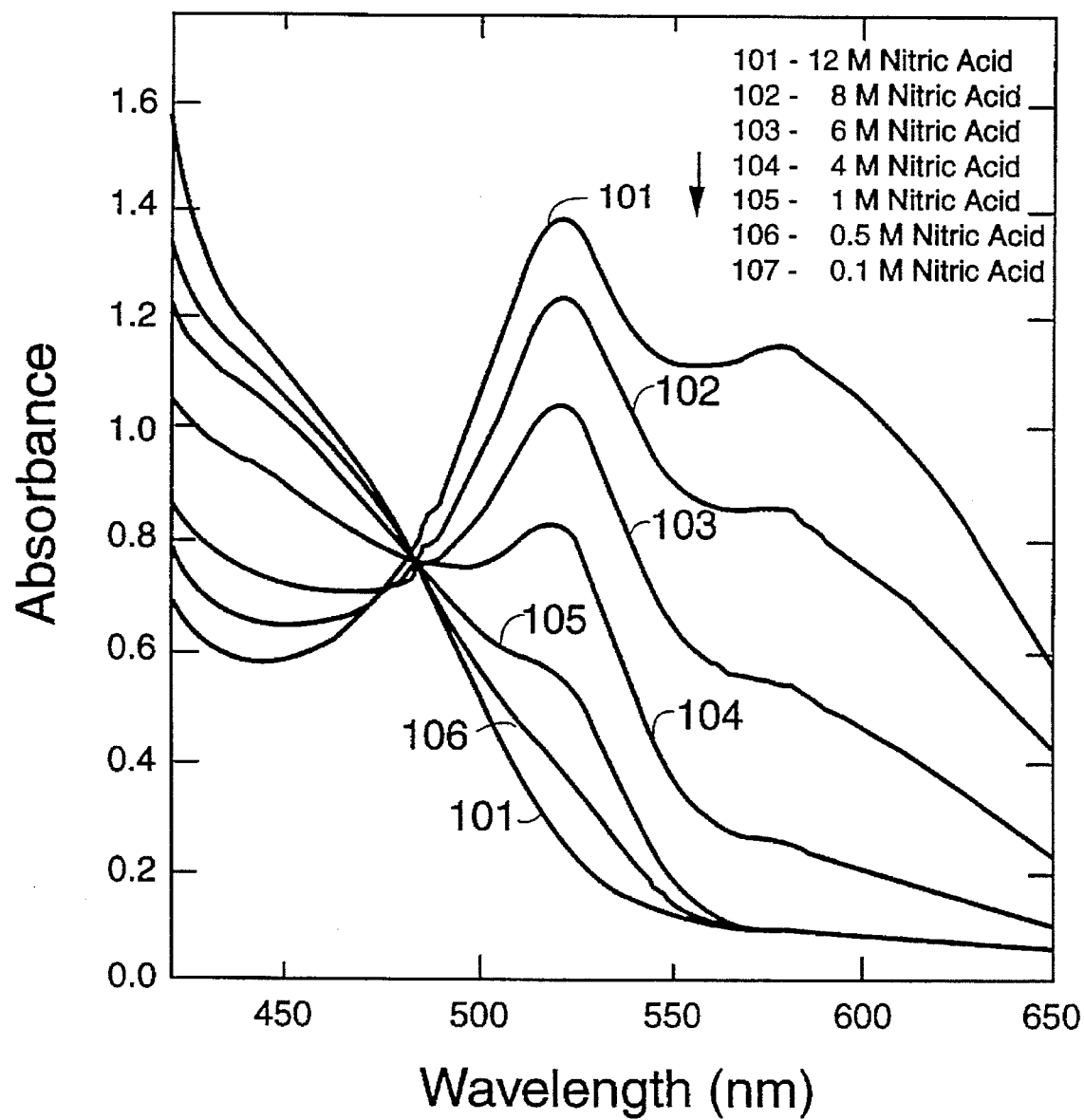
FIG. 10 is a graph of the absorbance versus wavelength for an acid sensor including both phenol red and brilliant yellow in polybenzimidazole, such absorbances at various acid concentrations.

Standard solutions of nitric acid can then be prepared and run for instrument calibration, i.e., development of a series of absorption traces for the various standard solutions, ranging from about 1 Molar about to about 12 Molar. Previous tests with various acid solutions placed upon a brilliant yellow/phenol red mixture in PBI coating, such a coating previously immobilized onto a quartz slide, show absorption spectrum peaks at about 520 nm and 570 nm, such peaks decreasing in intensity at lower acid concentrations. The results of analysis at various acid concentrations are shown in FIG. 10.

By use of the present apparatus and method the acidity of high molarity acid solutions can be determined for unknown solutions by comparison with developed standard absorptions and the method can be employed in the measurement of on-going processes to obtain real time analysis.

Although the present invention has been described with reference to specific details, it is not intended that such details should be regarded as limitations upon the scope of the invention, except as and to the extent that they are included in the accompanying claims.

What is claimed is:

1. An apparatus for determination of acid concentrations of a sample solution comprising:

a chamber for interrogation of a sample solution, the chamber having an inlet and outlet for the sample solution;

a fiber optic light source having a light emitting end for passing light transversely though the sample solution within the chamber, the fiber optic light source situated adjacent the chamber for interrogation of the sample solution;

a fiber optic collector having a light receiving end for receiving the light after transmission through the sample solution within the chamber, the fiber optic collector situated adjacent the chamber for interrogation of the sample solution;

a coating of an acid resistant polymeric composition upon at least one of either the light emitting end or the light receiving end, the polymeric composition in contact with the sample solution within the chamber and having a detectable response to acid concentrations within the range of about 0.1 Molar to about 16 Molar;

means for measuring the response of the polymeric composition in contact with the sample solution; and, means for comparing the measured response to predetermined standards whereby the acid molarity of the sample solution within the chamber can be determined.

2. The apparatus of claim 1 wherein said apparatus further includes a first lens attached to the end of the fiber optic light source, the first lens adapted to collimate light from the fiber optic light source and a second lens attached to the end of the fiber optic collector for focusing the collimated light after transmission through the chamber.

3. The apparatus of claim 2 wherein the polymeric composition is a polymer selected from the group consisting of poly(phenylquinoline), poly(biphenylquinoline), poly(benzobisthiazole), poly(phenylquinoxaline), and polybenzimidazole, said polymer including an indicator capable of undergoing colorimetric changes within the range of acid concentrations from about 0.1 Molar to about 16 Molar.

4. The apparatus of claim 3 wherein the indicator in combination with the polymer is a triarylmethane dye.

5. The apparatus of claim 2 wherein the polymeric composition is polybenzimidazole including an indicator capable of undergoing colorimetric changes within the range of acid concentrations from about 0.1 Molar to about 16 Molar.

6. The apparatus of claim 5 wherein the indicator in combination with the polybenzimidazole is a triarylmethane dye.

7. The apparatus of claim 5 wherein the indicator in combination with the polybenzimidazole is selected from the group consisting of phenolsulfonephthalein and substituted phenolsulfonephthaleins.

8. The apparatus of claim 7 wherein the indicator is selected from the group consisting of chrome azurol-S, phenolsulfonephthalein, 3',3"-dichlorophenolsulfonephthalein, or 5',5"-dibromo-ortho-cresolsulfonephthalein.

9. The apparatus of claim 5 wherein the indicator in combination with the polybenzimidazole is brilliant yellow.

10. The apparatus of claim 2 wherein the first and second lens are comprised of silica.

11. The apparatus of claim 2 further including a silane coupling agent situated between the lens and the polymeric composition.

12. An apparatus for determination of acid concentrations of a sample solution comprising:

a flow chamber for interrogation of a sample solution, the flow chamber having an inlet and outlet for the sample solution;

a fiber optic light source having a light emitting end for passing light transversely though the sample solution within the flow chamber, the fiber optic light source situated adjacent the flow chamber for interrogation of the sample solution;

a first lens attached to the end of the fiber optic light source, the first lens adpted to collimate light from the fiber optic light source;

a fiber optic collector having a light receiving end for receiving the collimated light after transmission through the sample solution within the flow chamber, the fiber optic collector situated adjacent the flow chamber for interrogation of the sample solution;

a second lens attached to the end of the fiber optic collector for focusing the collimated light after transmission through the sample solution within the flow chamber;

a coating of an acid resistant polymeric composition upon at least one lens, the polymeric composition in contact with the sample solution within the chamber and having a detectable response to acid concentrations within the range of about 0.1 Molar to about 16 Molar;

means for measuring the response of the polymeric composition in contact with the sample solution; and, means for comparing the measured response to predetermined standards whereby the acid molarity of the sample solution within the chamber can be determined.

13. A method of measuring the acid concentration of a sample solution comprising:

passing a portion of a sample solution into a chamber, the chamber having an inlet and outlet for the sample solution;

passing a light source through a fiber optic light source situated adjacent the chamber for interrogation of the sample solution and transversely through the sample solution within the chamber into a fiber optic collector situated adjacent the chamber for interrogation of the sample solution, wherein at least one of either the fiber optic light source or the fiber optic collector is coated upon a fiber end with a polymeric composition, the polymeric composition in contact with the sample solution within the chamber and having a detectable response to acid concentrations within the range of about 0.1 Molar to about 16 Molar;

measuring the response of the polymeric composition in contact with the sample solution; and, comparing the measured response to predetermined standards whereby the acid molarity of the sample solution within the chamber can be determined.

14. The method of claim 13 further including a first lens attached to the end of the fiber optic light source, the first lens adapted to collimate light from the fiber optic light source, and a second lens attached to the end of the fiber optic collector for focusing the collimated light after transmission through the chamber.

15. The method of claim 14 wherein the polymeric composition is a polymer selected from the group consisting of poly(phenylquinoline), poly(biphenylquinoline), poly (benzobisthiazole), poly(phenylquinoxaline), and polybenzimidazole, said polymer including an indicator capable of undergoing colorimetric changes within the range of acid concentrations from about 0.1 Molar to about 16 Molar.

16. The method of claim 15 wherein the indicator in combination with the polymer is a triarylmethane dye.

17. The method of claim 14 wherein the polymeric composition is polybenzimidazole including an indicator capable of undergoing colorimetric changes within the range of acid concentrations from about 0.1 Molar to about 16 Molar.

18. The method of claim 17 wherein the indicator in combination with the polybenzimidazole is a triarylmethane dye.

19. The method of claim 17 wherein the indicator in combination with the polybenzimidazole is selected from the group consisting of phenolsulfonephthalein and substituted phenolsulfonephthaleins.

20. The method of claim 19 wherein the indicator is selected from the group consisting of chrome azurol-S, phenolsulfonephthalein, 3',3"-dichlorophenolsulfonephthalein, or bromocresol-purple.

21. The method of claim 17 wherein the indicator in combination with the polybenzimidazole is brilliant yellow.

22. The method of claim 14 further including a silane coupling agent situated between the lens and the polymeric composition.

23. The method of claim 13 wherein the response of the polymeric composition to the acid concentration within the sample solution is a fluorescence emission by the polymeric composition.

24. The method of claim 13 wherein the response of the polymeric composition to the acid concentration within the sample solution is a colorimetric change by the indicator.

* * * * *